(12) United States Patent
Rodriguez

(10) Patent No.: US 9,113,942 B2
(45) Date of Patent: Aug. 25, 2015

(54) SURGICAL TOOL

(75) Inventor: William E. Rodriguez, Garfield, NJ (US)

(73) Assignee: Hospital for Special Surgery, New York, NY (US)

( * ) Notice: Subject to any disclaimer, the term of this patent is extended or adjusted under 35 U.S.C. 154(b) by 0 days.

(21) Appl. No.: 13/419,760

(22) Filed: Mar. 14, 2012

(65) Prior Publication Data

US 2013/0012971 A1    Jan. 10, 2013

Related U.S. Application Data

(60) Provisional application No. 61/466,094, filed on Mar. 22, 2011.

(51) Int. Cl.
*A61B 17/32* (2006.01)
*A61B 17/3209* (2006.01)
*A61B 19/00* (2006.01)

(52) U.S. Cl.
CPC ... *A61B 17/320016* (2013.01); *A61B 17/32002* (2013.01); *A61B 17/3209* (2013.01); *A61B 19/30* (2013.01); *A61B 2019/302* (2013.01); *A61B 2019/4857* (2013.01)

(58) Field of Classification Search
CPC ............... A61B 17/320016; A61B 17/32002; A61B 17/3209; A61B 19/30; A61B 2019/302; A61B 2019/4857
USPC ............... 606/167, 170, 181; 30/113.1, 162
See application file for complete search history.

(56) References Cited

U.S. PATENT DOCUMENTS

| | | | | |
|---|---|---|---|---|
| 4,791,928 A * | 12/1988 | Berke et al. | ............ | 606/180 |
| 4,887,598 A * | 12/1989 | Berke | ............ | 606/180 |
| 5,089,000 A * | 2/1992 | Agee et al. | ............ | 606/170 |
| 5,306,284 A * | 4/1994 | Agee et al. | ............ | 606/170 |
| 5,480,388 A * | 1/1996 | Zadini et al. | ............ | 604/157 |
| 5,582,617 A * | 12/1996 | Klieman et al. | ............ | 606/170 |
| 5,794,344 A * | 8/1998 | Poulos et al. | ............ | 30/113.1 |
| 5,817,119 A * | 10/1998 | Klieman et al. | ............ | 606/174 |
| 5,836,958 A * | 11/1998 | Ralph | ............ | 606/160 |
| 5,919,202 A * | 7/1999 | Yoon | ............ | 606/170 |
| 6,200,274 B1 * | 3/2001 | McNeirney | ............ | 600/562 |
| RE39,152 E * | 6/2006 | Aust et al. | ............ | 606/170 |
| 7,181,848 B1 * | 2/2007 | Tochtrop | ............ | 30/123 |
| 2007/0038236 A1* | 2/2007 | Cohen | ............ | 606/187 |
| 2007/0225740 A1* | 9/2007 | Suddaby | ............ | 606/170 |

* cited by examiner

*Primary Examiner* — Thomas McEvoy
*Assistant Examiner* — Julie A Szpira
(74) *Attorney, Agent, or Firm* — Beck Tysver Evans PLLC

(57) ABSTRACT

A surgical tool for use through laproscopic ports having improved haptic and tactile feedback.

1 Claim, 2 Drawing Sheets

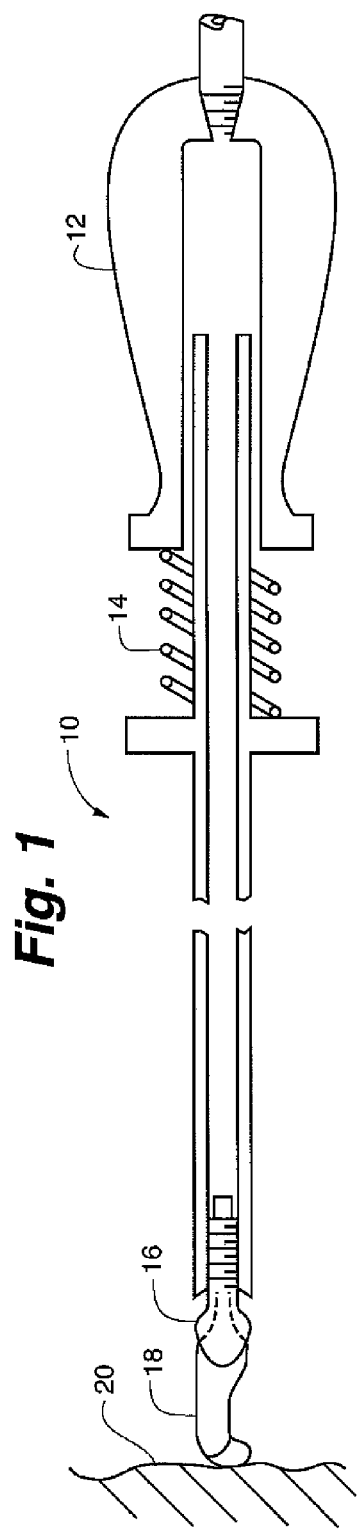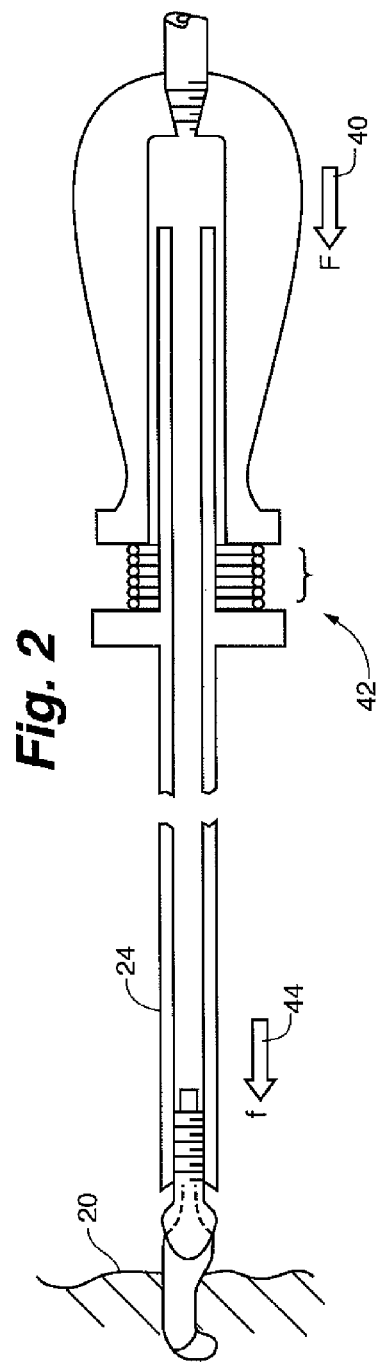

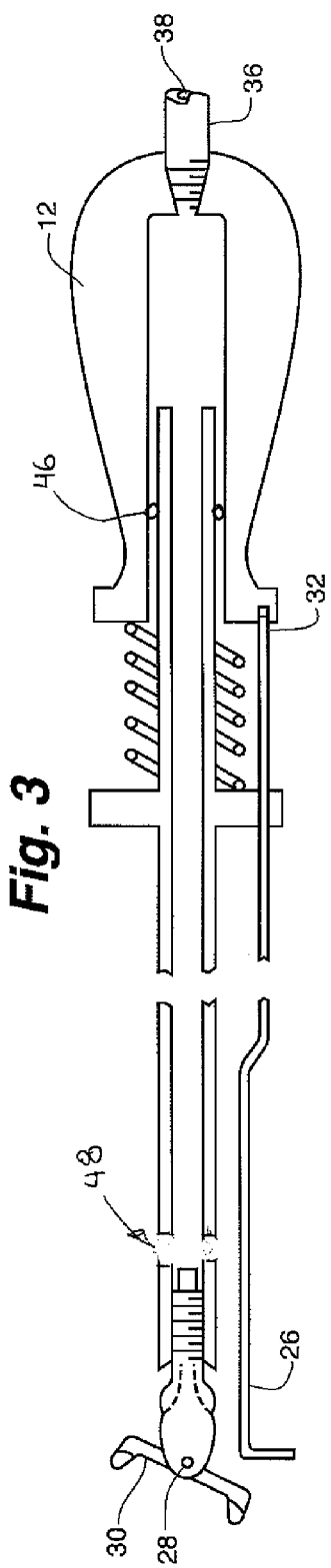

SURGICAL TOOL

FIELD OF THE INVENTION

The present invention relates generally to a surgical tool and more particularly to a tool that provides tactile feedback to the physician manipulating the tool.

BACKGROUND OF THE INVENTION

Bladed surgical tools such as scalpels are widely used for both open surgery and minimally invasive surgery. In the case of open surgery the angle of the bade and the position of the tool in the hands of the surgeon together supply the physician with direct knowledge of the properties of the tissue and blade interaction. However much of this surgical "feel" is lost when minimally invasive surgical approaches are undertaken, or when the geometry of the dissection forces the user to a remote hand position.

When surgical instruments are inserted through ports and observed with a camera much of the direct visual and tactile feedback is lost or reduced. This is a drawback to minimally invasive or laparoscopic surgeries.

For these reasons among others there is a need to improve the haptic properties of surgical tools.

BRIEF DESCRIPTION OF THE DRAWINGS

In the figures like reference numerals indicate identical structure, wherein:
FIG. 1 is a cross section of an embodiment of the tool;
FIG. 2 is a cross section of an embodiment of the tool; and,
FIG. 3 is a cross section of an embodiment of the tool.

DETAILED DESCRIPTION

The surgical tool 10 of the present invention as shown in FIG. 1 includes a pommel or handgrip that is manipulated by the surgeon. A relatively long shaft is coupled to the handle or handgrip 12 and it has a shaft 24 with a generally tubular shape to cooperate with access ports and the like. In some embodiments for example will have a fluid delivery. As is common, the tool can be advanced and retracted along a path defined in part by the location of the surgical intervention. The surgical blade 18 or other tool is located at the distal end of the shaft 24 of the tool 10 and fixed to the shaft with a conventional collet or coupler 16. Intermediate of the distal tool and the handgrip is a spring 14. The spring is mounted so that forces supplied by the physician act on the spring to compress it. The corresponding reaction forces are supplied by interaction with patient tissue. The motion associated with the compression of the spring is both observed and felt by the physician and these attribute restore some of the tactile sensations lost in the transition to modern forms of surgery. Most importantly, however, in the case of joint repair fairly substantial forces are applied to dissect tissue and cartilage. Awkward angles remote handgrip locations and indirect vision conspire to make tissue dissection difficult and fraught with risks. With the inventive surgical tool he physician has feedback about the mechanical properties of the tissue intersection with the distal tip. If "tough" tissue is encountered, the spring will compress as depicted at "D" in FIG. 2 and the motion and displacement will indicate that the tissue resists the cutting forces illustrated at 44. If relatively soft friable tissue 20 is encountered, then the spring will not compress or move indicating the tissue encountered is delicate.

In addition to the tactile or haptic improvement a visual feedback reference is also provided by a displacement guide 26 anchored in the handgrip 12 at location 32 as depicted in FIG. 3.

Although a blade 18 is illustrated other cutting elements are contemplated such as the articulated blade 30 adapted for motion about axis 28 as seen in FIG. 3. Other cutting tools include burrs and powered cutters. In these instances irrigation or suction may be applied to the surgical site through an appropriate connection to the tool as illustrated by suction or irrigation fitting 36 shown connected to the handgrip 12. Fluids maybe exchanged through the lumen 38 shown in FIG. 3. To facilitate sealing a rolling O-ring 46 or other seal may be supplied to control leakage from the tool. Apertures typified by aperture 48 may allow fluid to enter or exit the tool.

What is claimed is:

1. A surgical tool for use on a patient at a surgical site comprising:
   a hand grip;
   a telescopic shaft coupled to said handgrip said telescopic shaft having a distal end and a proximal end, and having an axis of the telescopic shaft;
   a rolling O-ring positioned between said telescopic shaft and said handle at said proximal end of said telescopic shaft;
   a coupler for coupling an articulated blade to said distal end of said telescopic shaft;
   said articulated blade mounted to rotate about an axis perpendicular to said axis of the shaft;
   a spring interposed between said handgrip and said articulated blade, whereby force supplied by a physician acting on said spring to compress it provides a visual feedback reference indicated by a displacement guide anchored in said hand grip;
   a fluid fitting having a lumen coupled to said handgrip and in fluid communication with at least one aperture proximate said articulated blade for exchanging fluids through said at least one aperture in said distal end of said telescopic shaft.

* * * * *